United States Patent [19]

Weber, II et al.

[11] 4,045,229
[45] Aug. 30, 1977

[54] NOVEL UV ABSORBING COMPOUNDS AND PHOTOGRAPHIC ELEMENTS CONTAINING UV ABSORBING COMPOUNDS

[75] Inventors: Wayne Woodrow Weber, II; Donald Warren Heseltine, both of Rochester, N.Y.

[73] Assignee: Eastman Kodak Company, Rochester, N.Y.

[21] Appl. No.: 641,788

[22] Filed: Dec. 18, 1975

Related U.S. Application Data

[63] Continuation-in-part of Ser. No. 506,913, Sept. 17, 1974, abandoned.

[51] Int. Cl.$^2$ ............................................. G03C 1/84
[52] U.S. Cl. ................................. 96/84 UV; 252/300; 350/1
[58] Field of Search ............... 96/84 UV; 252/300 U; 350/1

[56] References Cited

U.S. PATENT DOCUMENTS

| | | | |
|---|---|---|---|
| 3,052,636 | 9/1962 | Strobel | 96/84 UV |
| 3,125,597 | 3/1964 | Wahl et al. | 260/469 |
| 3,702,861 | 11/1972 | Howe | 252/300 |

FOREIGN PATENT DOCUMENTS 1,087,902  2/1961  Germany .............................. 96/84

OTHER PUBLICATIONS

Bredereck et al., Chem. Ber. 103, pp. 222–235, (1970).

*Primary Examiner*—John D. Welsh
*Attorney, Agent, or Firm*—J. G. Levitt

[57] ABSTRACT

1-Amino-4-cyano-1,3-butadiene compounds of the formula

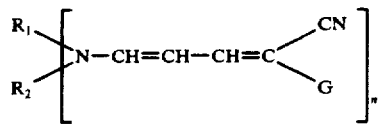

wherein $n$ is 1 or 2, when $n$ is 1 $R_1$ and $R_2$ can be the same or different and represent hydrogen, alkyl including substituted alkyl, aryl including substituted aryl or cyclic alkyl groups, except that both $R_1$ and $R_2$ cannot be hydrogen, or taken together $R_1$ and $R_2$ represent the elements necessary to complete a cyclic amino group and when $n$ is 2 at least one of $R_1$ and $R_2$ is alkylene or arylene; G represents an electron withdrawing group. The compounds are especially useful in photographic elements as UV absorbers.

19 Claims, No Drawings

NOVEL UV ABSORBING COMPOUNDS AND PHOTOGRAPHIC ELEMENTS CONTAINING UV ABSORBING COMPOUNDS

This is a continuation-in-part of our co-pending application Ser. No. 506,913, filed Sept. 17, 1974, now abandoned.

This invention relates to 1-amino-4-cyano-1,3-butadiene compounds useful as filter compounds and to photographic elements containing said compounds.

The compounds of the invention absorb ultraviolet (UV) light and have properties which make them useful filter dyes. Although the UV absorbing compounds of the invention appear to be primarily useful with respect to color films and papers containing photoreducible silver halide; if desired, they can be incorporated in black-and-white films which contain photo-reducible silver halide. They may also be used in other areas where protection from UV light is needed, such as in the plastics industry. Protection from UV light can be obtained by incorporating the UV absorbing compounds of this invention into the body of or the surface of the plastic item being protected.

As is known to those skilled in the photographic art silver halide emulsions are sensitive to ultraviolet light. Color films such as Kodachrome and Ektachrome Films, for example, would be adversely affected by ultraviolet light unless protected therefrom. To illustrate, if ultraviolet light is not substantially prevented from reaching the silver halide-containing layers of a color film, such as those just mentioned, the film will be more bluish than it should be. Snow and blacktop driveways, for example, would have an unnatural bluish cast or appearance in photographs made using film that has no UV absorbing filter layer.

From the foregoing brief discussion it will be apparent that to obtain color pictures of true color rendition, ultraviolet light should be prevented from reaching the silver halide-containing layers of the color film.

Various materials have been examined for use as UV absorbers in photographic elements, particularly in the overcoats of such elements. UV absorbers which are water-soluble may diffuse during coating and processing to other layers of the photographic element and thus can sometimes interfere with various photographic functions. On the other hand, when water-insoluble UV absorbers are evaluated, a cosolvent is usually required for dispersion into a photograhic emulsion and the resulting system is not always stable, i.e., an oil-phase often separates on standing. Upon coating, the dye aggregates, and the coated layer shows a new, unwanted absorption shoulder.

The prior art method of dispersing water-insoluble substances into an aqueous gelatin coating composition which was preferred heretofore involved dissolving the substance in (i) a high boiling organic solvent (which will not evaporate from the coated layer), and (ii) optionally with an auxiliary solvent, and then milling the solution with an aqueous gelatin solution in a colloid mill for a considerable time to produce a satisfactory coating composition. The dispersion then had to be noodled and washed to remove the auxiliary solvent. This was a complicated, time-consuming, inefficient, heat-generating process. Further, the resulting dispersions tended to coagulate, aggregate, or crystallize, and the oil in the coated layers derived therefrom tended to migrate or diffuse to other layers.

In one aspect this invention relates to a photographic element comprising a support having thereon at least one radiation sensitive silver halide emulsion layer and a 1-amino-4-cyano-1,3-butadiene ultraviolet absorbing compound.

In another aspect this invention relates to a photographic element comprising a support having thereon at least one radiation sensitive silver halide emulsion layer and an ultraviolet filter layer comprising a binder and at least one compound having the formula:

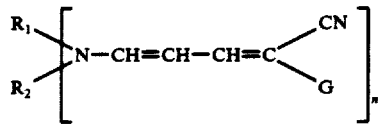

wherein n is 1 or 2, when n is 1, $R_1$ and $R_2$ can be the same or different and represent hydrogen, cyano, alkyl of 1 to 10 carbon atoms including substituted alkyl such as cyanoalkyl, alkoxyalkyl, aryl of 6 to 20, preferably of 6 to 10 carbon atoms including substituted aryl or cyclic alkyl groups of 5 or 6 carbon atoms, except that both $R_1$ and $R_2$ cannot be hydrogen, or taken together $R_1$ and $R_2$ represent the elements necessary to complete a cyclic amino group such as, for example, piperidino, morpholino, pyrrolidino, hexahydroazepino and piperazino groups, and when n is 2 at least one of $R_1$ and $R_2$ can be alkylene or arylene; G represents an electron withdrawing group. Any of the electron withdrawing groups known in the art can be used according to this invention. Preferred electron withdrawing groups include

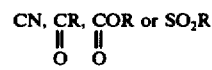

where R represents an alkyl group of 1 to 10 carbon atoms or an aryl group of 6 to 20, preferably 6 to 10 carbon atoms.

In yet another aspect, this invention relates to a photographic element comprising at least one silver halide emulsion layer coated on a film support, said film support having incorporated therein at least one ultraviolet filter compound of the formula:

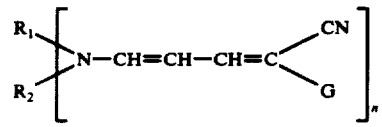

wherein n is 1 or 2, when n is 1, $R_1$ and $R_2$ can be the same or different and represent hydrogen, cyano, alkyl of 1 to 10 carbon atoms including substituted alkyl such as cyanoalkyl, alkoxyalkyl, aryl of 6 to 20, preferably of 6 to 10 carbon atoms including substituted aryl or cyclic alkyl groups of 5 or 6 carbon atoms, except that both $R_1$ and $R_2$ cannot be hydrogen, or taken together $R_1$ and $R_2$ represent the elements necessary to complete a cyclic amino group such as, for example, piperidino, morpholino, pyrrolidino, hexahydroazepino and piperazino groups, and when n is 2 at least one of $R_1$ and $R_2$ can be alkylene or arylene; G represents an electron withdrawing group such as

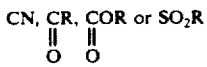

where R represents an alkyl group of 1 to 10 carbon atoms or an aryl group of 6 to 20, preferably 6 to 10 carbon atoms.

In still yet another aspect, this invention relates to novel ultraviolet absorbing compounds having the general formula:

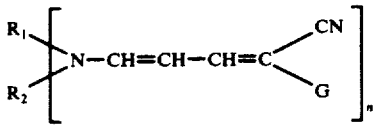

wherein $n$ is 1 or 2, when $n$ is 1, $R_1$ and $R_2$ can be the same or different and represent hydrogen, cyano, alkyl of 1 to 10 carbon atoms including substituted alkyl such as cyanoalkyl, alkoxyalkyl, aryl of 6 to 20, preferably of 6 to 10 carbon atoms including substituted aryl or cyclic alkyl groups of 5 or 6 carbon atoms, except that both $R_1$ and $R_2$ cannot be hydrogen, or taken together $R_1$ and $R_2$ represent the elements necessary to complete a cyclic amino group such as, for example, piperidino, morpholino, pyrrolidino, hexahydroazepino and piperazino groups, and when $n$ is 2 at least one of $R_1$ and $R_2$ can be alkylene or arylene; G represents an electron withdrawing group such as

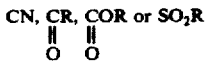

where R represents an alkyl group of 1 to 10 carbon atoms or an aryl group of 6 to 20, preferably 6 to 10 carbon atoms.

The new compounds of this invention are useful as ultraviolet filter absorbers which have high absorptive capability. Our UV absorbing compounds are generally low melting solids and are pure in the liquid state. The compounds of the present invention absorb strongly up to 400 nm. and have little absorption beyond 400 nm. They are unexpectedly stable when exposed to heat. In the liquid state they are hydrophobic, but may be incorporated directly into an otherwise conventional polymeric photographic support. Our compounds can also be used with a binder as a coating composition which can be coated onto a photographic support as a separate layer, without the use of special or auxiliary solvents if desired.

The reaction used in preparing the compounds of our invention is conventionally carried out by treating an appropriate primary or secondary amine with an appropriate intermediate in absolute alcohol at refluxing temperature of the resulting solution followed usually by distillation of the product under reduced pressure. The compounds are obtained in good yield and high purity.

In one form, the present invention is directed to a photographic support having incorporated therein at least one UV absorbing compound having the structure of formula 1. In order to use materials for UV protection of a photographic element when the materials are incorporated within the support, it is generally desirable that the support be transparent, and it is usually preferred that the support be substantially colorless. A variety of conventional transparent photographic film supports are known to the art into which the UV absorbing compounds of this invention can be incorporated. Photographic supports can be broadly categorized for purposes of this discussion into those that can be solvent cast and those that are formed from a melt. The UV absorbing compounds of this invention are stable and can be incorporated into the photographic element without use of a special or auxiliary solvent. To incorporate our UV absorbing compounds into a solvent-cast film support, such as a celulosic support—e.g., one composed of cellulose nitrate, cellulose diacetate, cellulose triacetate, etc.—it is merely necessary to dissolve the compound in the casting solution employed in the manufacture of the support. Our UV absorbing compounds can be incorporated into melt-formed polymeric film supports merely by dispersing the dye within the molten polymer. Since our UV absorbing compounds possess a surprising degree of thermal stability they can be incorporated into melt-formed film support materials such as polyalkylene (e.g. polyethylene), polystyrene, phthalic acid polyesters such as poly(ethylene terephthalate), polycarbonates as well as other, lower melting, resinous polymers useful in forming film supports. It is generally preferred that our UV absorbing compounds be substantially homogeneously dispersed within the film support so as to exhibit uniform optical density upon viewing the support. This can be readily achieved by thoroughly mixing the UV absorbing material with the support material (prior to its being formed into a support) using procedures well known in the art.

When the UV absorbing compound is coated onto a support rather than being incorporated therein, it is, of course, possible to employ any conventional photographic support. The support can be opaque to transparent. The support can have any one of a variety of diverse forms, such as a glass, metal, film, wood, paper or composite (e.g. resin coated paper) support. To immobilize spatially the UV absorbing material on the support it is generally preferred that the UV absorber be incorporated within a transparent layer containing a binder, which layer is directly associated with the support. Sometimes the binder can be the same type of polymer as that which comprises the support. The compound can also be incorporatd into any photographic binder layer as desired. Generally, any conventional transparent binder can be used. An especially useful class of binders are the latexes disclosed in Chen U.S. application Ser. No. 506,919 filed Sept. 17, 1974. In this Chen U.S. application is also disclosed a valuable method for incorporating the UV absorbing compounds of this invention into a photographic element or emulsion. Hydrophilic colloids such as gelatin can also be used as a binder material if desired. The binder layer(s) containing one or more of the UV absorbing compounds of this invention can be located directly on the support or can be separated by one or more undercoats provided for the purpose of improving adhesion to the support. Such binder layer(s) can also be present as overcoats or protective layers(s) overlying or between the light-sensitive emulsion layer(s) if desired. Binder layers containing one or more UV absorbing compound can be coated both as an underlayer as well as an overcoat layer on a single support if desired. Other suitable photographic vehicles useful as binders and layer arrangements are described in Product Licensing Index, Vol. 92, December 1971, publication 9232, page 108, paragraph VIII, here incorporated by reference. Generally, the UV absorbing compounds in the binder layer as contemplated herein are chosen to provide optical densities similar to those set forth above for UV absorbing compounds incorporated into the support. Optically homogeneous dispersion of the dye in the binder is preferred and can be obtained without the use of auxiliary solvents. This can be achieved by the techniques disclosed in the aforementioned Chen application as well as techniques which are well known to those skilled in the art.

This invention may be used with photographic elements which contain silver halide emulsions. The 1-amino-4-cyano-1,3-butadiene compounds may also be incorporated in the silver halide emulsion layer. The silver halide emulsions can comprise, for example, silver choride, silver bromide, silver bromoiodide, silver chlorobromide, silver chloroiodide, silver chlorobromoiodide crystals or mixtures thereof. The emulsions can be coarse or fine grain emulsions and can be prepared by a variety of techniques, e.g., single jet emulsions such as those described in Trivelli and Smith *The Photographic Journal*, Vol. LXXIX, May, 1939 (pp 330–338), double jet emulsions such as Lippmann emulsions, ammoniacal emulsions, thiocyanate or thioether ripened emulsions such as those described in Nietz et al U.S. Pat. No. 2,222,264 issued Nov. 19, 1940; Illingsworth U.S. Pat. No. 3,320,069 issued May 16, 1967 and McBride U.S. Pat. No. 3,271,157 issued Sept. 6, 1966. Silver halide emulsions can form latent images predominantly on the surface of the silver halide grains, or predominantly on the interior of the silver halide grains such as those described in Davey et al U.S. Pat. No. 2,592,250 issued May 8, 1952; Porter et al U.S. Pat. No. 3,206,313 issued Sept. 14, 1965; Berriman U.S. Pat. No. 3,367,778 issued Feb. 6, 1968 and Bacon et al U.S. Pat. No. 3,447,927 issued June 3, 1969. If desired, mixture of such surface and internal image-forming emulsions can be made, such as being described in Luckey et al. U.S. Pat. No. 2,996,382 issued Aug. 15, 1961. Silver halide emulsions can be regular grain emulsions such as the type described in Klein and Moisar, *J. Phot. Sci.*, Vol. 12, No. 5, September/October, 1964, pp. 242-251 and German Pat. No. 2,107,118. Negative type emulsions can be made, as well as direct positive emulsions as described in Leermakers U.S. Pat. No. 2,184,013 issued Dec. 19, 1939; Kendall et al U.S. Pat. No. 2,541,472 issued Feb. 13, 1951; Schouwenaars British Pat. No. 723,019 issued Feb. 2, 1955; Illingsworth et al French Pat. No. 1,520,821 issued Mar. 4, 1968; Illingsworth U.S. Pat. No. 3,501,307 issued Mar. 17, 1970 Ives U.S. Pat. No. 2,563,785 issued Aug. 7, 1951; Knott et al U.S. Pat. No. 2,456,953 issued Dec. 21, 1948 and Land U.S. Pat. No. 2,861,885 issued Nov. 25, 1958.

In one preferred form, the 1-amino-4-cyano-1,3-butadiene compounds may be used with elements designed for color photography, for example, elements containing silver halide emulsion and color-forming couplers such as those described in U.S. Pat. Nos. 2,376,679 by Frohlich et al., 2,322,027 by Jelley et al, 2,801,171 by Fierke et al., 2,698,794 by Godowsky, 3,227,554 by Barr et al. and 3,046,129 by Graham et al.; or elements to be developed in solutions containing color-forming couplers such as those described in U.S. Pat. Nos. 2,525,718 by Mannes et al., 2,592,243 by Carroll et al and 2,950,970 by Schwan et al.; and in false-sensitized color materials such as those described in U.S. Pat. No. 2,763,549 by Hanson.

In another form this invention may be used with elements such as described in U.S. Pat. No. 3,761,276 by Evans and in U.S. Pat. No. 2,716,059 by Yutzy et al; silver salt diffusion transfer systems wherein development of silver halide precedes solution of the silver halide with processes as described in U.S. Pat. Nos. 2,352,014 by Rott, 2,543,181 by Land, 3,020,155 by Yackel et al and 2,861,885 by Land; color image-transfer processes such as described in U.S. Pat. Nos. 3,087,817, 3,185,567 and 2,983,606 by Rogers, 3,253,915 by Weyerts et al., 3,227,550 by Whitmore et al., 3,227,551 by Barr et al., 3,227,552 by Whitmore, 3,415,644, 3,415,645 and 3,415,646, all by Land, 2,543,181 and 3,635,707, Canadian Pat. No. 674,082 and Belgian Pat. Nos. 757,959 and 757,960, both issued Apr. 23, 1971; and imbibition transfer processes as described in U.S. Pat. No. 2,882,156 by Minsk; all of which are incorporated herein by reference.

In photographic elements intended for use in color photography, the UV absorbing compounds of this invention are preferably used in a binder layer as an overcoat over the light-sensitive layer(s) to be protected. The UV absorbing compounds may also be used as an interlayer i.e. a layer provided under the layer(s) that do not require protection. The UV compounds may also be incorporated into the support or the support may be provided with a UV absorbing filter layer before the light-sensitive emulsion layer(s) are applied thereto in order to minimize the reflectance of light from the surface of the support or to protect the emulsion layer if the element is exposed through a transparent support.

The following examples further illustrate the invention.

PREPARATION OF INTERMEDIATES

A. The intermediate 3-acetanilidoallylidenemalononitrile

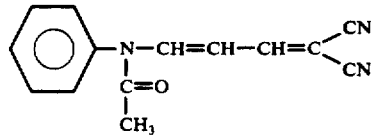

was prepared by heating at reflux for 10 minutes, malononitrile (50 g.) with 3-anilinoacroleinanil hydrochloride (186 g.) in acetic anhydride (600 ml.). The solution was then cooled and filtered and the solid washed in methanol. The product was recrystallized from acetic anhydride, filtered and the solid washed with methanol and dried. Yield 110 g.

B. The intermediate 3-methoxyallylidenemalononitrile

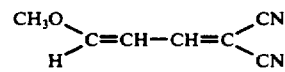

was prepared by heating at reflux of 1 hour malononitrile (132 g., 2.0 mole) and trimethoxypropene (270 g. 2.0 mole) in 250 ml. of butyronitrile. The solution was then cooled in dry ice and the product was obtained. Yield 65 g. 25%.

PREPARATION OF UV ABSORBING COMPOUNDS

A. 3-Dibutylaminoallylidenemalononitrile $$\begin{array}{c}C_4H_9\\C_4H_9\end{array}\!\!N-CH=CH-CH=C\begin{array}{c}CN\\CN\end{array}$$

Dibutylamine (15.0 g. 0.116 mole) was refluxed for 20 minutes with the intermediate of Example A 3-acetanilidoallylidenemalononitrile (11.9 g., 0.05 mole) in ethanol (50 ml.). The ethanol was then distilled off and the product obtained by distillation at 157° C and 3 $\mu$. M.W. 231.33 $C_{14}H_{21}N_3$, Yield 5.0 g. (45%).

B. 3-Dihexylaminoallylidenemalononitrile $$\begin{array}{c}C_6H_{13}\\C_6H_{13}\end{array}\!\!N-CH=CH-CH=C\begin{array}{c}CN\\CN\end{array}$$

Dihexylamine (20.0 g, 0.108 mole) was refluxed for 20 minutes with 3-acetanilidoallylidenemalononitrile (11.9 g, 0.05 mole) in ethanol (50 ml). The ethanol was then distilled off and the product obtained by distillation at 170° C at 5 $\mu$. M.W. 287.43, $C_{18}H_{29}N_3$, Yield 4.8 g (33%).

C. 3-Tert-butylaminoallylidenemalononitrile $$\begin{array}{c}CH_3\ \ H\\|\ \ \ \ |\\CH_3-C-\!\!-N-CH=CH-CH=C\begin{array}{c}CN\\CN\end{array}\\|\\CH_3\end{array}$$

Tert-butylamine (50 g, 0.68 mole) was refluxed for 15 minutes with 3-acetanilidoallylidenemalononitrile (6.0 g, 0.29 mole) in ethanol (300 ml). The compound precipitated from the reaction mixture after chilling and was purified by recrystallization from ethanol. M.W. 175.24, Yield 15.0 g. (30%).

D. 3-Diisobutylaminoallylidenemalononitrile $$\left(\begin{array}{c}CH_3\\|\\CH-CH_2\\|\\CH_3\end{array}\right)_2\!\!=N-CH=CH-CH=C\begin{array}{c}CN\\CN\end{array}$$

Diisobutylamine (25 g, 0.20 mole) was refluxed for 15 minutes with 3-acetanilidoallylidenemalononitrile (23.0 g, 0.10 mole) in ethanol (50 ml). The ethanol was then distilled off and the product obtained by distillation at 124°-160° and 4 $\mu$. M.W. 231.33, $C_{14}H_{21}N_3$, Yield 9.5 g (41%).

E. 3-Di-sec-butylaminoallylidenemalononitrile $$\left(\begin{array}{c}CH_3\\|\\C_2H_5-CH\end{array}\right)_2\!\!=N-CH=CH-CH=C\begin{array}{c}CN\\CN\end{array}$$

Di-sec-butylamine (25 g, 0.20 mole) was refluxed for 20 minutes with 3-acetanilidoallylidenemalononitrile (23.0 g, 0.10 mole) in ethanol (100 ml). The ethanol was then distilled off and the product obtained by distillation at 150° C and 6 $\mu$. M.W. 231.33, $C_{14}H_{21}N_3$, Yield 4.9 g (20%)

F. 3-Hexahydroazepinoallylidenemalononitrile $$\text{(hexahydroazepine ring)}-N-CH=CH-CH=C\begin{array}{c}CN\\CN\end{array}$$

Hexahydroazepine (20.0 g, 0.2 mole) was refluxed for 15 minutes with 3-acetanilidoallylidenemalononitrile (11.9 g, 0.05 mole) in ethanol (50 ml). The ethanol was then distilled off and the product obtained by distillation at 150°-180° at 3 $\mu$. M.W. 201.24, $C_{12}H_{15}N_3$, Yield 2.5 g (25%).

G. 3-N(n-butyl)-N-cyanomethyl aminoallylidenemalononitrile $$\begin{array}{c}C_4H_9\\ \\CH_2\\|\\CN\end{array}\!\!N-CH=CH-CH=C\begin{array}{c}CN\\CN\end{array}$$

N-butyl-N-cyanomethylamine (13 g.) was heated with the intermediate of Example B, 3-methoxyallylidenemalononitrile (13.4 g.). The solution was then distilled with the fraction boiling at 140°-172° at 8 $\mu$ collected. Yield 11.5 g.

The following compounds (H-L) were prepared using the intermediate of Example A with the following amines:
  (a) Bis(2,2-diethoxyethyl)amine
  (b) N-cyanomethyl-N-methylamine hydrochloride
  (c) Piperazine
  (d) N,N'-Diethyl-1,6-hexanediamine
  (e) Bis(2-cyanoethyl)amine

H. 3[N,N-Bis-(2,2-diethoxyethyl)amino]allylidenemalononitrile $$\begin{array}{c}(C_2H_5O)_2-CH-CH_2\\ \\(C_2H_5O)_2-CH-CH_2\end{array}\!\!N-CH=CH-CH=C\begin{array}{c}CN\\CN\end{array}$$

I. 3(n-methyl-N-cyanomethyl)aminoallylidenemalononitrile $$\begin{array}{c}NC-CH_2\\ \\CH_3\end{array}\!\!N-CH=CH-CH=C\begin{array}{c}CN\\CN\end{array}$$

J. 1,4-Piperazino bis(allylidenemalononitrile)

$$\begin{array}{c}NC\\|\\C=CH-CH=CH-N\\|\\NC\end{array}\text{(piperazine)}\begin{array}{c}CN\\|\\N-CH=CH-CH=C\\|\\CN\end{array}$$

K. N,N'-diethyl-N,N-di-(4,4-dicyanobutadienyl)-1,6-diaminohexane $$\begin{array}{c}NC\\|\\C=CH-CH=CH-N-(CH_2)_6-N-CH=CH-CH=C\\|\ \ \ \ \ \ \ \ \ \ \ \ \ \ \ \ \ \ \ \ \ \ \ \ \ \ |\ \ \ \ \ \ \ \ \ \ \ \ \ \ \ \ \ \ \ \ \ \ \ \ \ \ \ \ \ \ \ \ \ \ \ \ |\ \ \ \ \ \ \ \ \ \ \ \ \ \ \ \ \ \ \ \ \ \ \ \ \ \ \ \ \ \ \ \ \ \ \ \ \ \ \ \ \ \ \ \ \ \ |\\NC\ \ \ \ \ \ \ \ \ \ \ \ \ \ \ \ \ \ \ \ \ \ C_2H_5\ \ \ \ \ \ \ \ \ \ \ \ \ \ \ \ \ \ \ \ \ C_2H_5\ \ \ \ \ \ \ \ \ \ \ \ \ \ \ \ \ \ \ \ \ \ \ \ \ \ \ \ \ \ \ \ \ \ \ \ \ \ \ CN\end{array}$$

L. 3-[N,N-bis(2-cyanoethyl)amino]allylidenemalononitrile

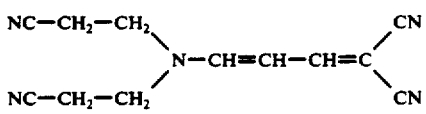

Compounds M-P were prepared by refluxing together three reactants, the appropriate amine, the appropriate sulfonylacetonitrile and 1,1,3-trimethoxypropene. The particular reactants used are in Table I below. Compounds N, O and P precipitated during refluxing or on subsequent cooling. Compounds N and O were treated with additional alcohol, ethanol or isopropanol, so that the precipitate could be filtered easily. Compound N was purified by dissolving the compound in cresol and reprecipitating it by addition of methanol. Compound O was purified by passing a methanol/acetonitrile solution of the compound through a column containing Amberlyst® ion exchange resin. Compound P was washed with ether and purified by redissolving the compound in acetone, adding ether until the solution turned cloudy, and then chilling the suspension for 72 hours before filtering off the purified compound. Compound M was more difficult to isolate. It did not precipitate directly from the reaction mixture. A portion of the reaction mixture was removed, stirred with ether until crystals formed and these were then used as seed crystals for the reaction mixture. Ethanol was added, the product was filtered off and recrystallized from methanol.

M. 3-Morpholinoallyidene methylsulfonylacetonitrile

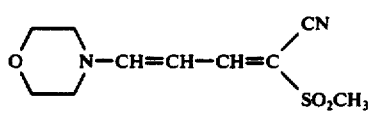

N. 3-Morpholinoallylidene 4-tert-butylphenylsulfonylacetonitrile

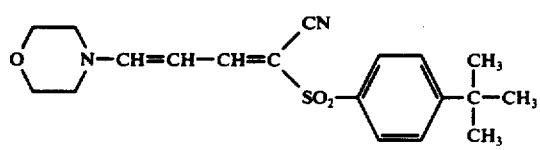

O. 3-Piperazinoallylidene 4-tert-butylphenylsulfonylacetonitrile

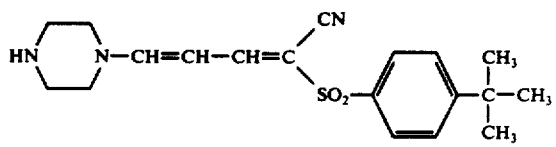

P. 3-N-methylpiperazinoallylidene 4-tert-butylphenylsulfonylacetonitrile

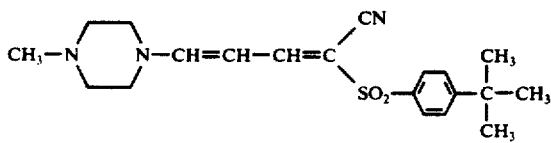

TAble 1

| Compound | Amine | Sulfonylacetonitrile |
|---|---|---|
| M | Morpholine | Methylsulfonylacetonitrile |
| N | Morpholine | 4-t-butylphenylsulfonylacetonitrile |
| O | Piperazine | 4-t-butylphenylsulfonylacetonitrile |
| P | N-Methylpiperazine | 4-t-butylphenylsulfonylacetonitrile |

Several of the UV absorbers of the preceding examples were mixed into a methanol solution and the absorption maxima ($\lambda$max) and extinction coefficients ($\epsilon$max) were calculated are listed in Table 2.

Table 2

| Example | Max (n.m.) | ($\epsilon$max) |
|---|---|---|
| A | 377 | $6.60 \times 10^4$ |
| B | 377 | $6.50 \times 10^4$ |
| C | 373 | $6.30 \times 10^4$ |
| D | 377 | $6.65 \times 10^4$ |
| E | 377 | $5.90 \times 10^4$ |
| F | 376 | $6.54 \times 10^4$ |
| H | 376 | $6.10 \times 10^4$ |
| I | 362 | $5.75 \times 10^4$ |
| M | 362 | $6.35 \times 10^4$ |
| N | 372 | $6.20 \times 10^4$ |
| O | 372 | $6.53 \times 10^4$ |
| P | 371 | $6.94 \times 10^4$ |

EVALUATION OF PHOTOGRAPHIC COATINGS

EXAMPLE 1

The UV compound of Example A above (3-dibutylaminoallylidenemalononitrile) was dispersed without auxiliary solvent in a gelatin emulsion and coated to obtain coverage of 0.98 g/m² of dry gel and 0.27 g/m² of UV compound. This layer was coated onto a cellulose acetate film support and the absorption ($\lambda$max) of the coating was found to be the same as in the methanol solution (377 nm).

EXAMPLE 2

The optical density of the U.V. compound of Example B (3-Dihexylaminoallylidenemalononitrile) was determined in a series of coatings. Example 2(b) was a no solvent/gelatin dispersion of the U.V. compound. Example 2(c) was a di-n-butyl phthalate/gelatin dispersion of the U.V. compound and Example 2(d) was a dispersion of the U.V. compound in the form of a loaded latex, whereby the U.V. compound is contained in the solid particles of a polymeric latex composition, prepared as disclosed in the aforementioned Chen U.S. Patent Application Ser. No. 506,919, filed Sept. 19, 1974. The dispersion of loaded latex particles was prepared by dissolving 40.0 g of 3-dihexylaminoallylidenemalononitrile in 700 cc. of acetone and then gradually stirring 1320 g. of the latex, poly(n-butyl methacrylate-co-2-acrylamido-2-methylpropane sulfonic acid-co-2-acetoacetoxy ethyl methacrylate (85:10:5), into the U.V. compound/solvent solution. The acetone was removed in 24 min. at 50° C. Example 2(a) was a coating of gelatin without the U.V. compound. The following optical densities were observed:

Table 3

| Example | Gelatin g/m² | Dye g/m² | Optical Densities 370 nm | 415 nm |
|---|---|---|---|---|
| 2(a) | 0.54 | — | 0.08 | 0.05 |
| 2(b) | 0.54 | 0.20 | 1.16 | 0.55 |
| 2(c) | 0.54 | 0.20 | 1.60 | 0.42 |

Table 3-continued

| Example | Gelatin g/m² | Dye g/m² | Optical Densities 370 nm | 415 nm |
|---|---|---|---|---|
| 2(d) | 0.54 | 0.20 | 3.00 | 0.11 |

The above data demonstrates that a coating of gelatin and especially the loaded latex form of the U.V. compound-containing composition provide excellent ultraviolet light absorbing properties with a very sharp cut-off at 415 nm at the same dye coverage.

EXAMPLE 3

A multilayer color negative coating was prepared as described in U.S. Pat. No. 3,046,129, column 25, line 67-column 26, line 20. Over the blue-sensitive layer of this coating was coated an ultraviolet absorbing layer, comprising a loaded latex of the compound of Example B in the latex of Example 2 (2.2 g in 40.0 g latex) prepared as described in Example 2. Sufficient gelatin was added to the dispersion so that the layer contained 0.11 g/m² UV compound and 0.90 g/m² gelatin. A protective gelatin overcoat was coated over the ultraviolet absorbing layer. A control coating, identical in all respects except that the ultraviolet absorbing layer was omitted, was prepared. Samples of the coatings were exposed in an Eastman 1B sensitometer to a simulated daylight light source with no filter. Other samples were exposed to the same light source through a Wratten 18A filter and still other samples were exposed through a Wratten 2A filter. The coatings were developed to color negatives in a process similar to that described in U.S. Pat. No. 3,046,129, column 23, line 35-column 24, line 24.

The Wratten 18A filter transmits only ultraviolet radiation and infrared radiation. The Wratten 2A filter absorbs ultraviolet radiation to 405 nm but transmits light at wavelengths beyond 405 nm. Table 4 shows the difference in sensitivity ($\Delta \log E$) of the blue-sensitive layer between the coating containing the ultraviolet absorbing compound and the coating without the absorbing compound.

There was no difference in log E values of the coating exposed through a Wratten 2A filter which shows that the ultraviolet compound is not absorbing visible light. The difference in log E values of coatings exposed through a Wratten 18A filter shows that the ultraviolet absorbing compound is absorbing ultraviolet light efficiently. The clear exposure shows that ultraviolet radiation contributes significantly to the exposure of the control, which exposure is undesirable for good color reproduction.

Table 4

| | Clear | Wratten 2A | Wratten 18A |
|---|---|---|---|
| $\Delta \log E$* | −0.14 | 0.00 | −1.85 |

*log exposure of blue-sensitive layer of experimental coating - log exposure of control.

Similarly, a UV compound according to this invention can be incorporated into the support of a multilayer color negative material with excellent UV protection obtainable.

The invention has been described in detail with particular reference to certain preferred embodiments thereof, but it will be understood that variations and modifications can be effected within the spirit and scope of the invention.

We claim:

1. In a photographic element comprising a support, at least one radiation sensitive silver halide emulsion layer and an ultraviolet absorbing compound, the improvement comprising the use of a 1-amino-4-cyano-1,3-butadiene ultraviolet absorbing compound.

2. The element according to claim 1 wherein said 1-amino-4-cyano-1,3-butadiene compound is of the formula:

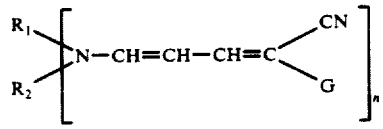

wherein n is 1 or 2, when n is 1, $R_1$ and $R_2$ are independently chosen to represent hydrogen, an alkyl group of 1 to 10 carbon atoms, an aryl group of 6 to 20 carbon atoms, or a cyclic alkyl group of 5 or 6 carbon atoms provided that $R_1$ and $R_2$ cannot both be hydrogen, or $R_1$ and $R_2$ taken together represent the atoms necessary to complete a cyclic amino group and when n is 2 at least one of $R_1$ and $R_2$ is alkylene or arylene, and G represents an electron withdrawing group.

3. A photographic element comprising a support having thereon at least one radiation sensitive silver halide emulsion layer and an ultraviolet filter layer comprising a binder and at least one compound having the formula:

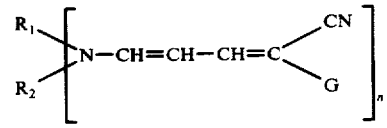

wherein n is 1 or 2, when n is 1, $R_1$ and $R_2$ are independently chosen to represent hydrogen, an alkyl group of 1 to 10 carbon atoms, an aryl group of 6 to 10 carbon atoms, or a cyclic alkyl group of 5 or 6 carbon atoms provided that $R_1$ and $R_2$ cannot both be hydrogen, or $R_1$ and $R_2$ taken together represent the atoms necessary to complete a cyclic amino group and when n is 2 at least one of $R_1$ and $R_2$ is alkylene or arylene, and G represents an electron withdrawing group.

4. A photographic element according to claim 3 wherein the binder is a hydrophillic colloid.

5. A photographic element according to claim 3 wherein the electron withdrawing group is selected from the group consisting of

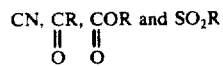

where R represents an alkyl group of 1 to 10 carbon atoms or aryl group of 6 to 10 carbon atoms.

6. A photographic element according to claim 3 wherein G is the group CN and $R_1$ and $R_2$ are both alkyl groups of 1 to 10 carbon atoms.

7. A photographic element according to claim 3 wherein G is the group CN, $R_1$ is hydrogen and $R_2$ is an alkyl group of 1 to 10 carbon atoms.

8. A photographic element comprising a support having thereon at least one silver halide emulsion layer and at least one ultraviolet filter layer comprising a binder and at least one compound selected from the group consisting of 3-dibutylaminoallylidenemalononitrile, 3-dihexylaminoallylidenemalononitrile, 3-tert-butylaminoallylidenemalononitrile, 3-diisobutylaminoallylidenemalononitrile, 3-di-sec-butylaminoallylidenemalononitrile, 3-hexahydroazepinoallylidenemalononitrile, 3-N-(n-butyl)-N-cyanomethyl aminoallylidenemalononitrile, 3[N,N-bis-(2,2-diethoxyethyl)amino]allylidenemalononitrile, 3(n-methyl-N-cyanomethyl)aminoallylidenemalononitrile, 1,4-piperazino bis(allylidenemalononitrile), N,N'-diethyl-N,N-di(4,4-dicyenobutadienyl)-1,6-diaminohexane and 3[N,N-bis(2-cyanoethyl)amino]allylidenemalononitrile.

9. A photographic element comprising a support having thereon at least one silver halide emulsion layer and at least one ultraviolet filter layer comprising a binder and at least one compound selected from the group consisting of 3-morpholinoallylidene methylsulfonylacetonitrile, 3-morpholinoallylidene 4-tert-butylphenylsulfonylacetonitrile, 3-piperazinoallylidene 4-tert-butylphenylsulfonylacetonitrile and 3-N-methylpiperazinoallylidene 4-tert-butylphenylsulfonylacetonitrile.

10. A photographic element comprising at least one silver halide emulsion layer coated on a film support, said film support being selected from a solvent cast or melt-formed film support and having incorporated therein at least one ultraviolet filter compound of the formula:

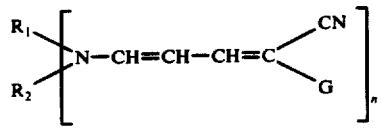

wherein $n$ is 1 or 2, when $n$ is 1, $R_1$ and $R_2$ are independently chosen to represent hydrogen, an alkyl group of 1 to 10 carbon atoms, an aryl group of 6 to 10 carbon atoms, or a cyclic alkyl group of 5 or 6 carbon atoms provided that $R_1$ and $R_2$ cannot both be hydrogen, or $R_1$ and $R_2$ taken together represent the atoms necessary to complete a cyclic amino group and when $n$ is 2 at least one of $R_1$ and $R_2$ is alkylene or arylene, and G represents an electron withdrawing group.

11. A photographic element according to claim 10 wherein the electron withdrawing group is selected from the group consisting of

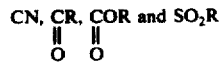

where R represents an alkyl group of 1 to 10 carbon atoms or aryl group of 6 to 10 carbon atoms.

12. A photographic element according to claim 10 wherein G is the group CN and $R_1$ and $R_2$ are alkyl groups of 1 to 10 carbon atoms.

13. A photographic element according to claim 10 wherein G is the group CN, $R_1$ is hydrogen and $R_2$ is an alkyl group of 1 to 10 carbon atoms.

14. A photographic element comprising at least one silver halide emulsion layer coated on a film support, said film support being selected from a solvent-cast or melt-formed film support and said support having therein at least one ultraviolet filter compound selected from the group consisting of 3-dibutylaminoallylidenemalononitrile, 3-dihexylaminoallylidenemalononitrile, 3-tert-butylaminoallylidenemalononitrile, 3-diisobutylaminoallylidenemalononitrile, 3-di-sec-butylaminoallylidenemalononitrile, 3-hexahydroazepinoallylidenemalononitrile, 3-N(n-butyl)-N-cyanomethyl aminoallylidenemalononitrile, 3(N,N-bis-(2,2-diethoxyethyl)amino]allylidenemalononitrile, 3(n-methyl-N-cyanomethyl)aminoallylidenemalononitrile, 1,4-piperazino bis(allylidenemalononitrile), N,N'-diethyl-N,N-di-(4,4-dicyanobutadienyl)-1,6-diaminohexane and 3-[N,N-bis(2-cyanoethyl)amino]allylidenemalononitrile.

15. A photographic element comprising at least one silver halide emulsion layer coated on a film support, said film support being selected from a solvent-cast or melt-formed film support and said support having therein at least one ultraviolet filter compound selected from the group consisting of 3-morpholinoallylidene methylsulfonylacetonitrile, 3-morpholinoallylidene 4-tert-butylphenylsulfonylacetonitrile, 3-piperazinoallylidene 4-tert-butylphenylsulfonylacetonitrile and 3-N-methylpiperazinoallylidene 4-tert-butylphenylsulfonylacetonitrile.

16. A photographic element comprising a support having thereon at least one silver halide emulsion layer and at least one ultraviolet filter layer comprising a binder and 3-dibutylaminoallylidenemalononitrile.

17. A photographic element comprising a support having thereon at least one silver halide emulsion layer and at least one ultraviolet filter layer comprising a binder and 3-dihexylaminoallylidenemalononitrile.

18. A photographic element comprising at least one silver halide emulsion layer coated on a film support, said film support being selected from a solvent-cast or melt-formed film support and having therein the ultraviolet filter compound 3-dibutylaminoallylidenemalononitrile.

19. A photographic element comprising at least one silver halide emulsion layer coated on a film support, said film support being selected from a solvent-cast or melt-formed film support and having therein the ultraviolet filter compound 3-dihexylaminoallylidenemalononitrile.

* * * * *